US00PP15033P3

(12) United States Plant Patent
Bourne

(10) Patent No.: US PP15,033 P2
(45) Date of Patent: Jul. 27, 2004

(54) GRAPE PLANT NAMED '13-29-281'

(50) Latin Name: *Vitis vinifera*
Varietal Denomination: 13-29-281

(75) Inventor: Timothy F. Bourne, Visalia, CA (US)

(73) Assignee: Sunview Vineyards of California, Inc., Delano, CA (US)

( * ) Notice: Subject to any disclaimer, the term of this patent is extended or adjusted under 35 U.S.C. 154(b) by 68 days.

(21) Appl. No.: 10/295,192

(22) Filed: Nov. 15, 2002

(65) Prior Publication Data

US 2004/0098770 P1 May 20, 2004

(51) Int. Cl.[7] ..... A01H 5/00

(52) U.S. Cl. ..... Plt./205

(58) Field of Search ..... Plt./205

*Primary Examiner*—Kent Bell
(74) *Attorney, Agent, or Firm*—Jondle & Associates PC

(57) ABSTRACT

This new grape plant '13-29-281' is new and different because of its very high sugar level at ripening, its very large berry size and good storage characteristics. It differs from other late ripening grapes such as 'Crimson Seedless' (not patented) by being much more productive when spur pruned, having less vigorous vegetative growth and having a much larger berry when gibberellic acid is applied to the vine. It differs from the '3-14-71 grapevine' (U.S. Plant Pat. No. 8,297) by having a larger berry with crisper berry flesh and from the 'Ralli Seedless' (U.S. Plant Pat. No. 9,865) by being much later in ripening with a more elongate berry.

2 Drawing Sheets

Genus and species: *Vitis vinifera.*

BACKGROUND AND SUMMARY OF THE INVENTION

The new grape plant '13-29-281' is of *Vitis vinifera* parentage and resulted from a twenty year breeding program which had as its goal the development of a late-ripening, brightly colored, red, seedless table grape. The female, seed parent (unnamed and unpatented) resulted from a series of crosses involving 'Emperor', (unpatented) 'Thompson Seedless' (unpatented), 'Hunisa' (unpatented), and 'Nocera' (unpatented). The male parent of the cross is an unnamed seedless grapevine resulting from a series of crosses involving 'Red Muscatel' (unpatented), 'Emperor' (unpatented), 'Nocera' (unpatented), and 'Hunisa' (unpatented). The hybridization resulting in '13-29-281' was made near McFarland, Calif. in 1992. The seedling was selected from a population of 11 seedlings of like parentage in 1995. The new selection was then propagated by cuttings and grafting to 'Freedom' (unpatented) rootstock. Those resulting plants proved stable and typical of the original seedling grapevine.

COMPARISON WITH PARENTAL CULTIVARS

The new grapevine variety, cv. '13-29-281' somewhat resembles '3-14-71' grapevine which it shares a similar pedigree. It differs from the '3-14-71' grapevine (U.S. Plant Pat. No. 8,297) by having a larger berry with crisper berry flesh and from the 'Ralli Seedless' (U.S. Plant Pat. No. 9,865) by being much later in ripening with a more elongate berry. '13-29-281' differs from its female parent by bearing stenospermic (seedless) fruit. '13-29-281' differs from its male parent by having red skinned berries as opposed to the green skinned berries of the male parent.

DESCRIPTION OF THE FIGURES

The accompanying drawings illustrate the following.

DETAILED BOTANICAL DESCRIPTION OF THE INVENTION

Figure 1:
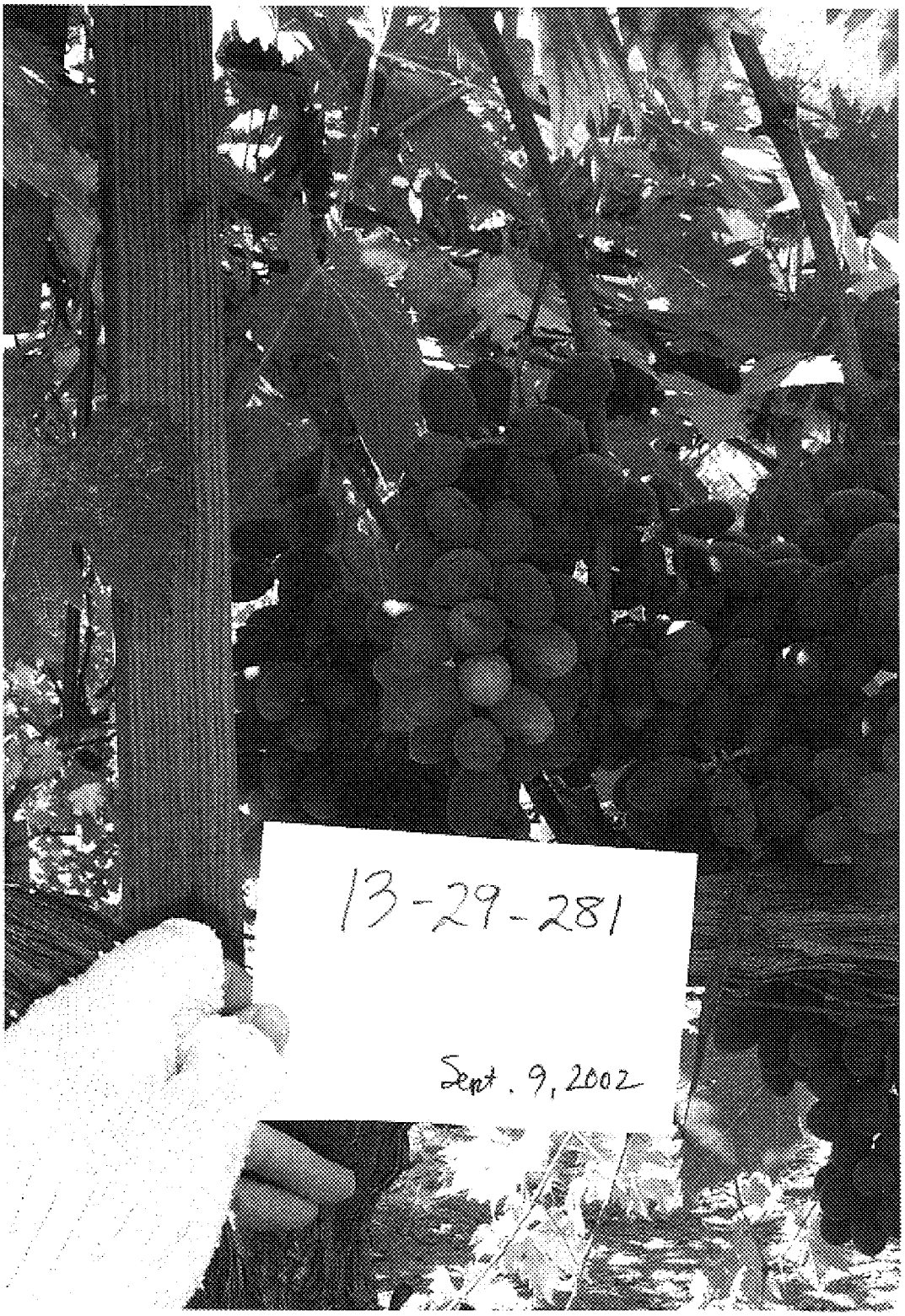
FIG. 1 shows a fruit cluster at harvest.
Figure 2:
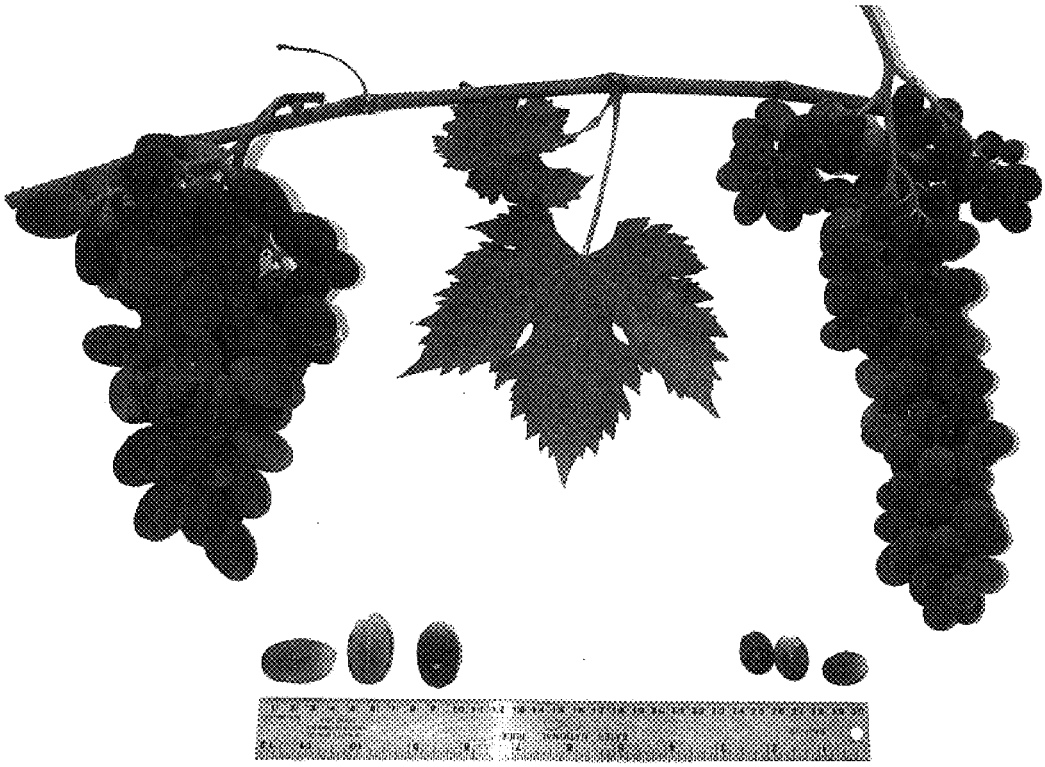
FIG. 2 shows the cane, leaf, natural fruit cluster (right) and fruit cluster following gibberellic acid applications (left).

The following description of grape plant '13-29-281' contains references to color names taken from the Munsell Color Chart for Plant Tissues, published by Munsell Color, New Windsor, N.Y. Descriptors used herein conform to those set forth by the International Board for Plant Genetic Resources Institute Grape Descriptors (Vitis spp.) of 1983 and/or 1997 which were developed in collaboration with the Office International de la Vigne et du Vin (OIV) and the International Union for the Protection of New Varieties of Plants (UPOV) and published in Descriptors for Grapevine (Vitis spp) (Anonymous, International Plant Genetic Resources Institute, ISBN 92--9043-352-3).

Descriptions of the new invention apply to vines of '13-29-281' grown on 'Freedom' rootstock at a density of 1,537 vines per hectare grown in Kern County, Calif. in 2001. These vines were in their first year of full production having been planted in 1998. These descriptions are believed to apply generally to the new variety grown under similar circumstances elsewhere:

VINE

General:

*Size.*—Large.

*Vigor.*—Medium, canes averaging 252 cm of growth when spur pruned and thinned to an average of 32 shoots per vine.

*Density of foliage.*—Moderate.

*Productivity.*—Very productive when spur pruned, up to 57,639 kg./hectare.

*Hardiness.*—Observed hardiness to 0C.

*Rootstock.*—'Freedom'.

Trunk:
*Size.*—Medium.
*Straps.*—Long, split.
*Surface texture.*—Shaggy.
*Inner bark color.*—2.5YR 5/6.
*Outer bark color.*—5YR 5/2.
*Trunk circumference.*—17.0 cm. at 1 meter height on 3.5 year old vines.

LEAVES

Mature leaves:
*Average blade length.*—15.4 cm.
*Average blade width.*—18.2 cm.
*Size of blade.*—Medium to large.
*Shape.*—Pentagonal.
*Anthocyanin coloration of main veins on the upper side of the blade.*—Absent.
*Mature leaf profile.*—Flat.
*Leaf margin.*—Lobed, doubly serrate, undulating.
*Blistering surface of blade upper surface.*—Absent.
*Leaf blade tip.*—In plane of the leaf.
*Undulation of margin.*—Slight.
*Apex.*—Narrowly acuminate.
*Thickness.*—Medium.
*Undulation of blade between main and lateral veins.*—Slight.
*Shape of teeth.*—Both sides convex.
*Length of teeth.*—5–15 mm.
*Ratio length/width of teeth.*—About 1.5:1, length: width.
*Leaf base.*—Sagittate.
*General shape of petiole sinus.*—Variable — half open to closed.
*Tooth at petiole sinus.*—Absent.
*Petiole sinus limited by veins.*—Absent.
*Shape of upper lateral sinus.*—Lobes slightly overlapping.
*Prostrate hairs between veins on lower surface of blade.*—Absent.
*Erect hairs between hairs on lower surface of blade.*—Absent.
*Prostrate hairs on main veins on lower surface of blade.*—Absent.
*Density of erect hairs on main veins on lower surface of blade.*—Sparse, confined to union of main veins.
*Prostrate hairs on main veins on upper surface of blade.*—Absent.

Upper surface:
*Summer color.*—5 GY 5/8 to 5/10.
*Autumn color.*—2.5Y 8/12.
*Surface texture.*—Smooth.
*Surface appearance.*—Dull.
*Goffering of blade.*—Absent.

Lower surface:
*Summer color.*—5GY 6/6 to 6/8.
*Autumn color.*—2.5Y 8/6.
*Anthocyanin coloration of main veins on lower leaf surface.*—Absent.
*Glossiness.*—Low.
*Pubescence.*—Absent.
*Surface texture.*—Smooth.
*Surface appearance.*—Dull.

Petiole:
*Length of petiole.*—13.3 cm.
*Diameter.*—5 mm.
*Length of petiole compared to middle vein.*—Slightly shorter.
*Density of prostrate hairs on petiole.*—Absent.
*Density of erect hairs on petiole.*—Absent.
*Shape of base of petiole sinus.*—Mostly closed, inside outline is ovate.
*Color of petiole.*—7.5GY 7/8.

TENDRILS

*Number.*—Numerous, opposite most leaves above the fifth node.
*Shape.*—Circular in cross section.
*Length.*—25 cm.
*Diameter.*—2 mm.
*Texture.*—Smooth.
*Color.*—2.5GY 7/8.

WOODY SHOOT

Canes:
*Shape.*—Broadly elliptical.
*Internode length.*—About 14.5 cm.
*Width at node.*—About 19 mm.
*Cross section.*—Circular.
*Surface.*—Smooth.
*Main color.*—5YR 5/6.
*Lenticels.*—Inconspicuous.
*Erect hairs on nodes.*—Absent.
*Erect hairs on internodes.*—Absent.
*Growth of axillary shoots.*—*Prolific.*

Laterals:
*Shape.*—Circular in outline.
*Number.*—Numerous. Most lateral buds produce a shoot above the 3rd node.
*Length.*—Variable, 25–150 cm.
*Diameter.*—7–10 mm.
*Internode length.*—Variable, 2.5–15 cm.
*Color.*—5YR 5/6.

Buds:
*Shape.*—Conical.
*Length.*—9 mm.
*Width.*—4 mm.
*Height.*—7 mm.
*Cane bud fruitfulness.*—Basal buds fruitful, 1–2 clusters per shoot.
*Time of bud burst.*—Mar. 22, 2003.

FLOWERS

General:
*Flower sex.*—Perfect.
*Length of first inflorescence.*—21.1 cm.
*Position of first flowering nodes.*—$4^{th}$ to $5^{th}$ node.
*Number of inflorescences per shoot.*—Usually 1 per shoot.
*Date of full bloom.*—May 9, 2001 in McFarland, Calif.
*Pedicel length.*—3.5 mm.
*Calyptra color.*—5GY 7/8.
*Ovary length.*—2 mm.
*Ovary color.*—5GY 4/8.
*Filament length.*—2 mm.
*Filament color.*—2.5GY 8/2.
*Anther length.*—2 mm.
*Anther color.*—2.5GY 8/8.

FRUIT

General:
*Ripening period.*—Late, about 2 weeks following 'Thompson Seedless' in the Delano, Calif. area.
*Date of ripening.*—About Aug. 24, 2001.
*Use.*—Fresh market.
*Keeping quality.*—Very good.

*Resistance.*—Insects — typical of *Vitis vinifera.* Diseases — typical of *Vitis vinifera.*
*Shipping quality.*—Good.
*Date of first harvest.*—Aug. 24, 2001.
*Solids-sugar.*—High, about 20 brix at full maturity.
*Refractometer test.*—21.0 brix.

Cluster:
*Bunch size.*—Medium.
*Bunch length* (*peduncle excluded*).—About 23.5 cm.
*Bunch width.*—About 12 cm.
*Bunch weight* (*natural*).—574 g.
*Bunch weight* (*gibberellic acid treated*).—1,340 g.
*Bunch density.*—Medium, loose.
*Number of berries.*—125.
*Form.*—Elliptical.

Peduncle:
*Length of peduncle.*—4 cm.
*Lignification of peduncle.*—Strong, entire peduncle to shoulder branch.
*Color.*—5YR 5/8.

Berry:
*Size.*—Medium.
*Uniformity of size.*—Variable.
*Berry weight* (*natural*).—5.2 g.
*Berry weight* (*gibberellic acid treated*).—8.7 g.
*Shape.*—Narrow elliptic.
*Presence of seeds.*—Seedless; 1 or 2 soft, rudimentary traces less than 1 mm in length found occasionally.
*Cross section.*—Circular.
*Dimensions.*—Longitudinal axis about 2.1 cm.; horizontal axis about 1.8 cm.
*Skin color* (*without bloom*).—5R 3/6 to 3/10.
*Coloration of flesh.*—Translucent, 2.5GY 8/2.
*Juiciness of flesh.*—Very juicy.
*Berry firmness.*—Very firm.
*Particular flavor.*—Neutral, typical vinifera.
*Bloom* (*cuticular wax*).—Medium.
*Pedicel length.*—7.5 mm.
*Berry separation from pedicel.*—Moderate.

Skin:
*Thickness.*—Medium.
*Texture.*—Tender.
*Reticulation.*—Absent.
*Roughness.*—Absent.
*Tenacity.*—Tenacious to flesh.
*Tendency to crack.*—Resistant.

What is claimed is:

1. A new and distinct variety of grape plant named '13-29-281' as herein illustrated and described.

* * * * *

MZI Selection 13-29-281